(12) United States Patent
Goebel et al.

(10) Patent No.: US 7,068,754 B2
(45) Date of Patent: Jun. 27, 2006

(54) SYSTEM TO GENERATE THERAPEUTIC RADIATION

(75) Inventors: Herbert Goebel, Munich (DE); Manfred Richard Schuster, Munich (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 149 days.

(21) Appl. No.: 10/610,853

(22) Filed: Jun. 30, 2003

(65) Prior Publication Data

US 2004/0264644 A1     Dec. 30, 2004

(51) Int. Cl.
*H05G 2/00* (2006.01)

(52) U.S. Cl. .......................................... 378/119; 378/84
(58) Field of Classification Search ................... 378/64, 378/65, 84, 119, 145, 147, 149, 85; 250/505.1
See application file for complete search history.

(56) References Cited

U.S. PATENT DOCUMENTS

| 2,638,554 A | 5/1953 | Maclaughlin et al. ....... 378/147 |
| 3,898,455 A | 8/1975 | Furnas, Jr. .................... 378/85 |
| 5,493,599 A | 2/1996 | Mattson ....................... 378/147 |
| 5,744,813 A | 4/1998 | Kumakhov ............... 250/505.1 |
| 6,442,236 B1 * | 8/2002 | Utaka .......................... 378/84 |

FOREIGN PATENT DOCUMENTS

| DE | 101 39 384 A1 | 3/2003 |
| EP | 1 195 177 A1 | 4/2002 |
| EP | 0 883 136 B1 | 9/2002 |

OTHER PUBLICATIONS

MM Western Europe, "Manufacturing Drilling", Apr. 2000, pp. 24-26.

* cited by examiner

*Primary Examiner*—Courtney Thomas

(57) ABSTRACT

Some embodiments include a ring anode to emit radiation, and a conical monochromator to monochromatize the emitted radiation. According to some aspects, an outer diameter of the ring anode is greater than an outer diameter of a base of the monochromator.

74 Claims, 8 Drawing Sheets

SYSTEM TO GENERATE THERAPEUTIC RADIATION

BACKGROUND

1. Field

The present invention relates generally to the generation of radiation, and more particularly to systems for delivering such radiation for therapeutic purposes.

2. Description

According to conventional radiation therapy, a radiation beam is directed toward a tumor located within a patient. The radiation beam delivers a predetermined dose of therapeutic radiation to the tumor according to an established therapy plan. The delivered radiation kills cells of the tumor by causing ionizations within the cells. In this regard, radiation therapy systems are designed to maximize radiation delivered to the tumor while minimizing radiation delivered to healthy tissue.

A conventional radiation therapy system utilizes X-radiation energies in excess of 1 MeV. State-of-the-art therapy systems generate this "MegaVolt X-Radiation" (MVR) using linear accelerators. In contrast, tube-based X-ray systems generate "KiloVolt X-Radiation" (KVR) having photon energies roughly between 20 keV to 200 keV. These KVR systems have long have been used for imaging and for other purposes. KVR systems may be much cheaper, simpler and more reliable than the linear accelerators used in MVR systems. Environmental safety is also of less concern with KVR systems, which typically require 3 mm of lead shielding as opposed to the 2 m of concrete shielding required for MVR systems.

Despite the foregoing advantages of KVR, MVR is often preferred for therapeutic use because of the high-energy electrons created by Compton scattering of MVR. Most tissue damage caused by KVR results from photoelectric absorption. Particularly in the case of low-energy KVR (photon energy<20 keV), damage resulting from photoelectric absorption is greatest at the surface of a radiation/tissue interaction and decreases with depth into the tissue. Consequently, a KVR beam of uniform or decreasing flux density (i.e., a divergent beam) may cause greater tissue damage at a patient's skin than at a therapy area within the patient's body.

Several existing techniques attempt to address this drawback of KVR therapy. A KVR therapy system such as those described in U.S. Pat. No. 6,366,801 to Cash et al uses a point radiation source which produces a divergent beam of traditional medical X-rays having energies in the kilovoltage range and focuses the beam on a target using a lens designed for this purpose. By focusing the radiation onto the target, the energy per unit area increases with proximity to the target. As a result, tissue damage at a portion of the target is greater than tissue damage at a same-sized portion of the radiation/skin interaction site. Efforts to increase the target-to-skin dose ratio include the development of lenses for focusing the radiation at greater angles of convergence and/or the injection of radiation-absorbing contrast agents at the target.

Also proposed are methods in which a patient is positioned, a target is irradiated by a radiation beam, the patient is repositioned such that a subsequent radiation beam would intercept an area of the patient's skin that was not irradiated by the previous radiation beam, and the target is irradiated again. The patient may be repositioned and the target irradiated several times. Still other methods include moving the radiation beam so as to scan the target. None of these existing techniques have proved to be satisfactorily efficient and/or effective in providing therapeutic KVR.

SUMMARY

To address the foregoing, some embodiments provide a ring anode to emit radiation, and a conical monochromator to monochromatize the emitted radiation. In some aspects, an outer diameter of the ring anode is greater than an outer diameter of a base of the monochromator.

In some embodiments, the present invention provides a radiation source to emit radiation from at least a first location and a second location, the first and second locations being separated by a first distance, and a monochromator comprising a surface of diffracting material, the surface comprising a third location and a fourth location separated by a second distance, the second distance being less than the first distance. The third location is to receive the radiation emitted from the first location and the fourth location is to receive the radiation emitted from the second location.

Embodiments may provide a radiation source to release radiation and one or more blocking devices to substantially block the radiation except for a portion of the radiation traveling along a substantially convergent three-dimensional path.

The claimed invention is not limited to the disclosed embodiments, however, as those of ordinary skill in the art can readily adapt the teachings herein to create other embodiments and applications.

BRIEF DESCRIPTION OF THE DRAWINGS

The exact nature of the claimed invention, as well as its objects and advantages, will become readily apparent from consideration of the following specification as illustrated in the accompanying drawings, in which like reference numerals designate like parts, and wherein:

DETAILED DESCRIPTION

The following description is provided to enable any person of ordinary skill in the art to make and use the claimed invention and sets forth the best modes contemplated by the inventors for carrying out the claimed invention. Various modifications, however, will remain readily apparent to those in the art.

Figure 1:
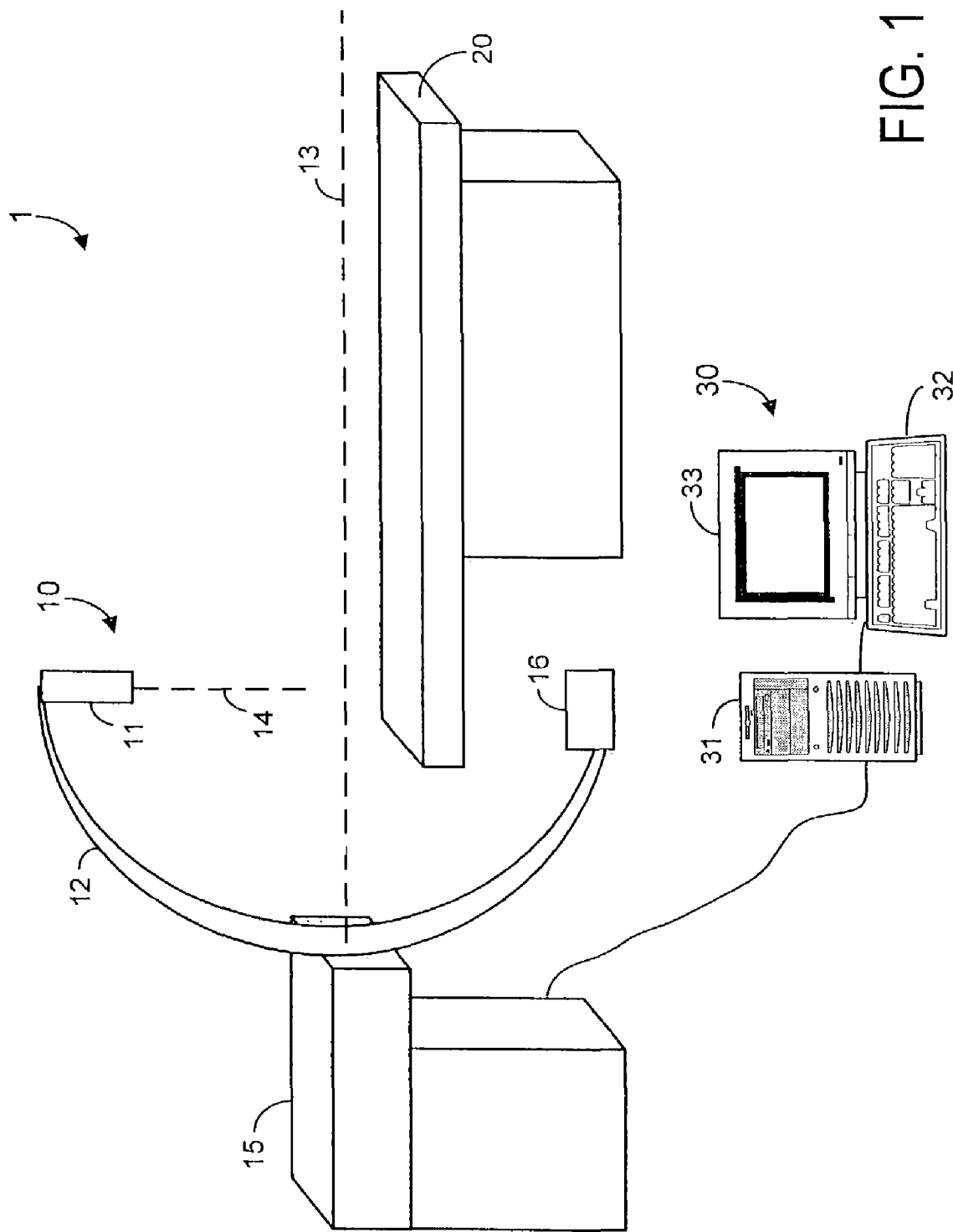
FIG. 1 is a diagram illustrating a radiation therapy room according to some embodiments.

FIG. 1 illustrates radiation therapy room 1 pursuant to some embodiments of the claimed invention. Radiation therapy room 1 includes KVR therapy unit 10, therapy table 20 and operator station 30. The elements of radiation therapy room 1 are used to deliver KVR to a patient according to a therapy plan. In this regard, KVR refers herein to any radiation having energies ranging from 20 to 200 keV. However, it should be noted that some embodiments may be used in conjunction with any radiation.

Therapy unit 10 is used to deliver therapeutic radiation to a target area through therapy head 11. Therapy head 11 includes a radiation source to emit KVR. KVR may include photon radiation having energies from 20 to 200 keV. Other types of radiation may be used in conjunction with some embodiments, including but not limited to neutron radiation such as thermal neutron radiation.

According to some embodiments, therapy head 11 may include a ring anode to emit radiation, and a conical monochromator to monochromatize the emitted radiation. In some embodiments, an outer diameter of the ring anode is greater than an outer diameter of a base of the monochromator. Further details of therapy head 11 according to some embodiments will be described below.

C-arm 12 is slidably mounted on base 13 and can therefore be moved in order to change the position of therapy head 11 with respect to table 20 and, more particularly, with respect to a patient lying on table 20. In some embodiments, c-arm 12 provides therapy head 11 with several degrees of freedom relative to a patient lying on table 20. These degrees of freedom may include translation along axis 13, rotation around axis 13, rotation around an axis perpendicular to the geometric center of c-arm 12, and translation along axis 14 of therapy head 11. Each of these degrees of freedom may assist in positioning a focal point of therapy head 11 at a desired target.

Base 15 may include one or more voltages sources such as high-voltage generators for supplying power used by therapy head 11 to generate KVR. Many c-arm/base configurations may be used in conjunction with some embodiments, including configurations in which base 15 is rotatably mounted to a ceiling of room 1, configurations in which one c-arm is slidably mounted on another c-arm, and configurations incorporating multiple independent c-arms.

Examples of c-arm KVR units include Siemens SIREMOBIL™, MULTISTAR™, BICOR™ and POLYSTAR™ units as well as other units designed to perform tomography and/or angiography. These units are often less bulky and less costly than MVR systems. Of course, any system for emitting radiation may be used in conjunction with some embodiments.

Imaging system 16 produces an image based on radiation emitted by therapy head 11. The image reflects the attenuative properties of objects located between therapy head 11 and imaging system 16 while the radiation is emitted. Imaging system 16 may comprise a camera-based or a flat panel-based imaging system.

A patient is placed on therapy table 20 during therapy in order to position a target between therapy head 11 and imaging system 16. Accordingly, table 20 may comprise mechanical systems for moving itself with respect to unit 10.

Operator station 30 includes processor 31 in communication with an input device such as keyboard 32 and an output device such as operator display 33. Operator station 30 is typically operated by an operator who administers actual delivery of radiation therapy as prescribed by an oncologist.

Each of the devices shown in FIG. 1 may include less or more elements than those shown. In addition, embodiments of the claimed invention are not limited to the devices described herein.

Figure 2:
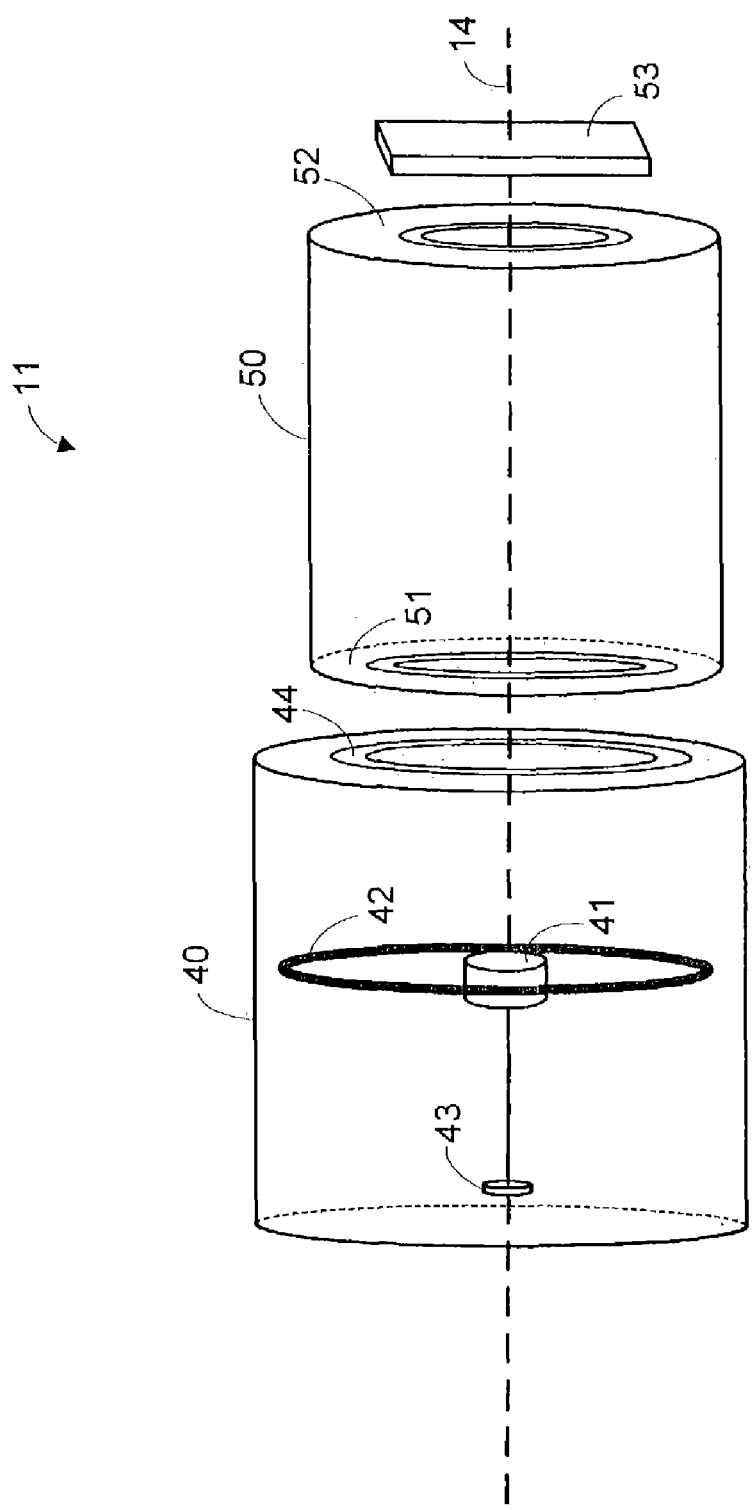
FIG. 2 is a cut away view illustrating internal elements of a therapy head according to some embodiments.
Figure 3:
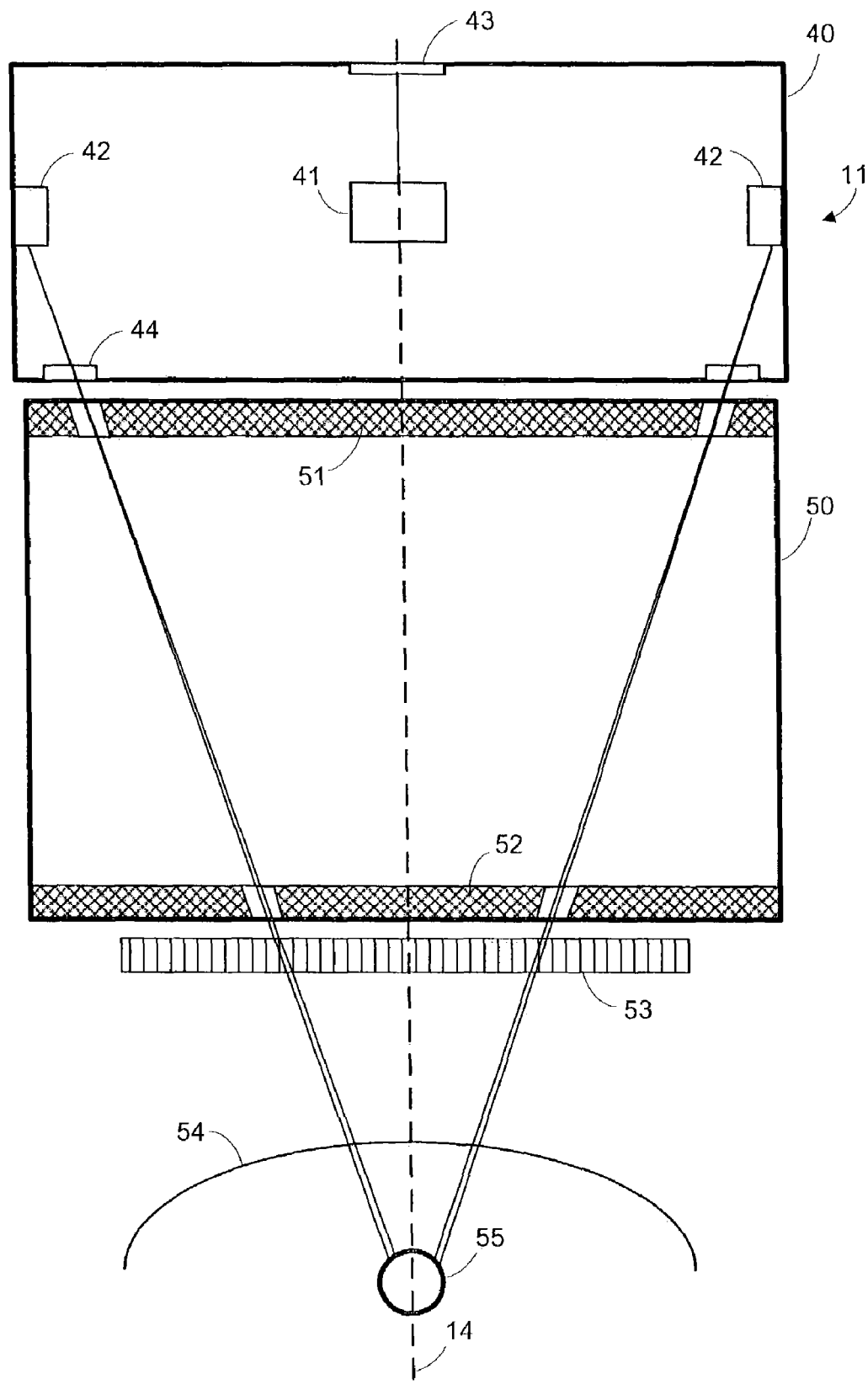
FIG. 3 is a longitudinal cross-section illustrating internal elements of a therapy head according to some embodiments, the therapy head including an annular anode, a monochromator, blocking devices, and filters.

FIG. 2 is a cut away view and FIG. 3 is a longitudinal cross-sectional view of therapy head 11 according to some embodiments. These views include pictorial representations of some elements of therapy head 11 and illustrate some relationships therebetween. Neither the elements nor their physical relationships to one another are necessarily drawn to scale.

Therapy head 11 of the present embodiment includes a photon radiation source and other elements arranged to provide radiation to a target at a sufficiently large angle of convergence. In particular, vacuum tube 40 of therapy head 11 includes cathode 41 and anode 42. Cathode 41 may comprise tungsten or any suitable material for emitting electrons. Cathode 41 may be used in conjunction with a Wehnelt cylinder to control and focus electrons emitted therefrom.

Anode 42 of FIG. 2 is ring-shaped and may also comprise tungsten. A radius of anode 42 may measure from 75 mm to 100 mm in order to produce X-ray radiation having a 30° angle of convergence and a beam path of 200 mm to 300 mm.

In operation, cathode 41 receives power in the form of a 120–200 kV tube voltage from high-voltage connector 43, which is coupled to a high-voltage source (not shown), while anode 42 is held at a high positive potential with respect to cathode 41. The received power heats cathode 41, and electrons are ejected from a surface of cathode 41 via thermal emission. The electrons are attracted to and accelerated by the high positive potential of anode 42.

The electrons impact anode 42 and produce X-rays both as characteristic radiation and Bremsstrahlung. Although only particular bundles of X-rays are illustrated in FIG. 3, X-rays are emitted isotropically from locations throughout ring anode 42. The spectrum of the characteristic radiation comprises sharp lines at discrete photon energies. The actual photon energies depend upon the material of which anode 42 is composed. For example, the dominant characteristic X-ray energy of tungsten is 59.3 keV and the dominant characteristic X-ray energy of thorium is 93.3 keV.

According to some embodiments, a radiation source comprises an anode such as ring anode 42 and a ring cathode. In other embodiments, a radiation source includes a ring anode and a plurality of cathodes, each located at a different position adjacent to ring anode 42. Moreover, anodes used in conjunction with some embodiments may possess any suitable shape. Some embodiments include a cathode adapted to move along a circumference of ring anode 42 while transmitting electrons thereto A radiation source according to some embodiments may comprise a conventional electron gun adapted to move along a circular path at high frequency. In some embodiments, a radiation source may include more than one radiation source. These sources may be adapted to move along a continuous path while emitting radiation from several locations on the continuous path. These sources may be fixed at locations delineating a shape, such as a circle or a polygon.

Exit window 44 maintains a vacuum within tube 40 but also allows photons to pass with high transmittivity. Window 44 may comprise a ring-shaped sheet of beryllium, aluminum, copper, and/or another material. In addition to the functions mentioned above, aluminum and copper provide filtering of photons having energies significantly lower than the characteristic energy of anode 42.

The portion of radiation that passes through window 44 subsequently intercepts housing 50. Housing 50 includes blocking devices 51 and 52. Blocking device 51 defines an opening for allowing a portion of radiation from exit window 44 to pass therethrough. The portion may comprise a portion of radiation traveling along a substantially convergent three-dimensional path. The portion in some embodiments forms a conical shell with a convergence angle of approximately 30° after passing blocking device 51. Blocking device 51 also comprises blocking material to substantially block radiation other than the portion of radiation.

"Conical" as used herein refers to an area or volume comprising any portion of a cone such as a single cone lobe, a cross section of a cone taken perpendicular to the major axis and of any thickness, an outer surface of a portion of a cone having a particular thickness, and/or any other portion. Moreover, the term "portion" may refer to the entirety or a subset of an element to which the term refers.

The portion of radiation that passes through blocking device 51 arrives at blocking device 52, which also comprises an opening for allowing a portion of the arriving radiation to pass therethrough. Blocking device 52 also comprises blocking material to substantially block radiation other than the portion of radiation from passing. In some embodiments, the portions of radiation passing through blocking devices 51 and 52 travel along a substantially convergent three-dimensional path. Accordingly, the relative positions of anode 42, blocking device 51, and blocking device 52 define the substantially convergent three-dimensional path. The illustrated path defines a hollow conical volume, however radiation according to different embodiments may travel along differently-shaped paths.

Filter 53 receives radiation that passes through blocking device 52. As shown in FIG. 3, the filtered radiation passes through patient surface 54 before reaching target 55. Filter 53 may comprise any material for substantially filtering out low-energy radiation from the received radiation. According to the example of FIG. 3, filtering low-energy radiation may decrease tissue damage occurring at locations on patient surface 54 and/or between patient surface 54 and target 55. Moreover, the convergent path of the filtered radiation may provide a greater dose per unit volume in target 55 than in other patient volumes.

Figure 4:
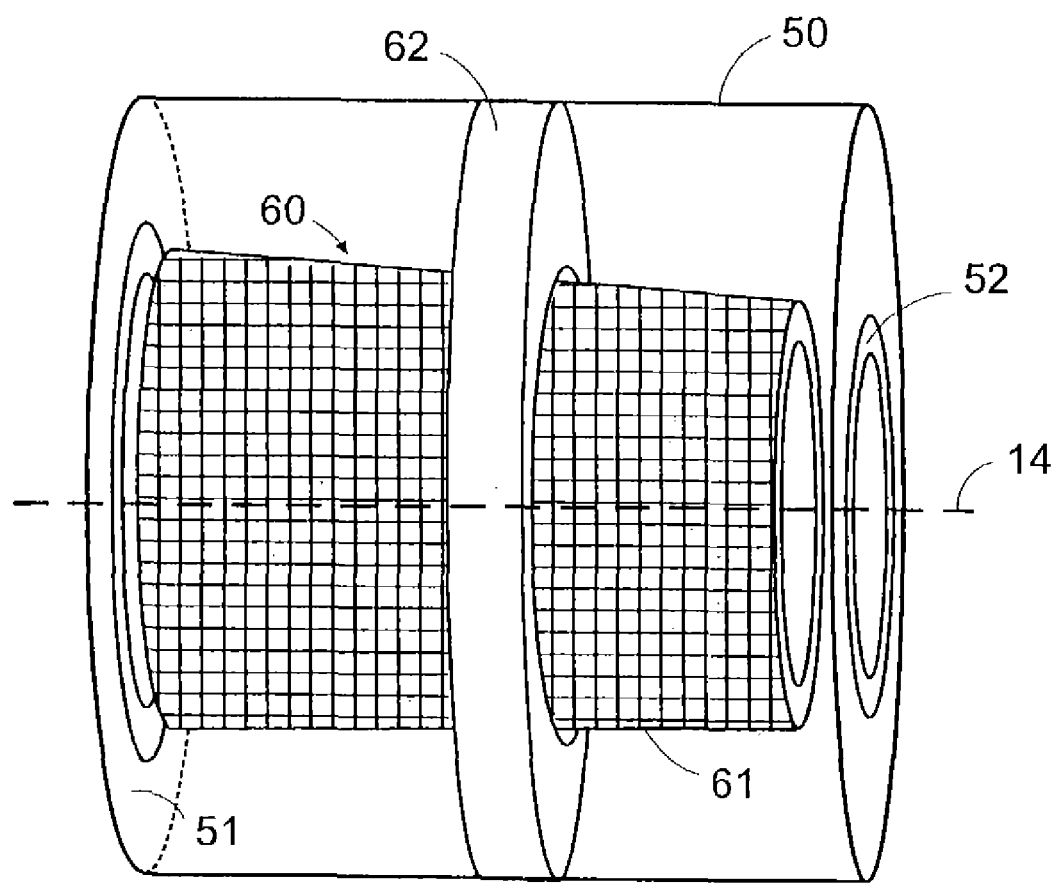
FIG. 4 is a cut away view illustrating internal elements of a monochromator housing according to some embodiments.
Figure 5:
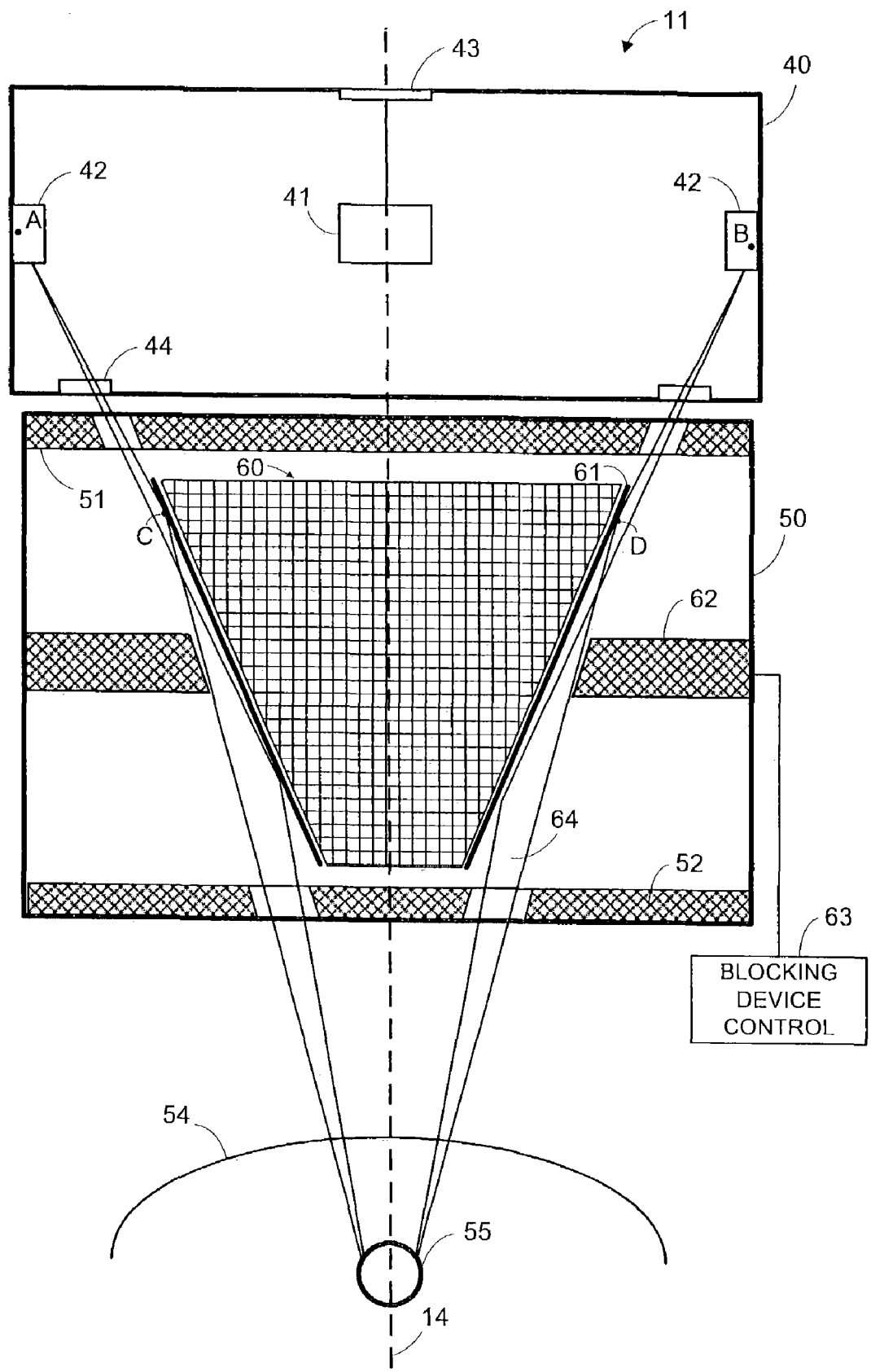
FIG. 5 is a longitudinal cross-section illustrating internal elements of a therapy head according to some embodiments, the therapy head including an annular anode and a monochromator with one external conical reflector surface.

FIG. 4 illustrates a cut away view of monochromator 60 disposed within housing 50 according to some embodiments. FIG. 5 shows a longitudinal cross-section of monochromator 60 in conjunction with a view of some other elements of therapy head 11. Monochromator 60 monochromatizes radiation received from tube 40 through blocking device 51.

Monochromator 60 is conical according to some embodiments. According to the illustrated example, an outer diameter of ring anode 42 is greater than a largest outer diameter of monochromator 60. In this regard, the largest outer diameter of monochromator 60 is equal to a diameter of a base of monochromator 60. A longitudinal cross-section through the illustrated monochromator is a straight line.

Monochromator 60 may comprise other rotationally symmetric shapes, including but not limited to a cylinder, a toroid, an ellipsoid, paraboloids, and logarithmic spirals of rotation. These rotationally symmetric shapes can be approximated by corresponding shapes on multi-sided base areas. For example, cones may be approximated by multi-sided pyramids.

Monochromator 60 includes conical outer surface 61. Surface 61 consists of crystalline material such as Highly Oriented Pyrolitic Graphite (HOPG). Other well-oriented crystalline materials include but are not limited to beryllium, aluminum, gold, platinum, LiF, and mica, which are known to provide high reflectivity to X-ray radiation.

Blocking device 62 may block direct radiation that is not monochromatized by monochromator 60 from reaching target 55. Blocking device 62 defines an opening that is coaxial with axis 14 of monochromator 60. Blocking device 62 may be movable along axis 14. Moreover, the conical opening has a diameter slightly larger than a diameter of monochromator 60 at areas where monochromator 60 is surrounded by blocking device 62. Accordingly, a diameter of the conical opening increases if blocking device 62 is moved toward vacuum tube 40.

Blocking device control 63 may control movement of blocking device 62 along axis 14 of monochromator 60. Blocking device control 63 may comprise one or more of software, hardware, and firmware elements located in one or more of processor 31, therapy head 11, base 13, a stand-alone device, or another device.

In operation, anode 42 emits radiation isotropically as described above. FIG. 5 illustrates particular bundles of the emitted radiation that pass through exit window 44 and blocking device 51 and intercept surface 61. Radiation emitted from anode 42 may follow a substantially convergent path to surface 61. For example, radiation emitted from locations A and B of anode 42 is received at locations C and D of surface 61, respectively, and a distance between locations C and D is less than a distance between locations A and B. In some embodiments, the angle of convergence is between 25° and 35°.

Window 44 and blocking device 51 may be designed to pass radiation that thereafter intercepts diffracting material of surface 61 at a particular angle of incidence. This angle of incidence may be substantially equal to a Bragg angle corresponding to the material and to a desired radiation energy. In particular, a corresponding Bragg angle is equal to $\sin^{-1}(\lambda/(2*d))$, wherein d is the lattice plane distance of the diffracting material and $\lambda$ is the wavelength (which is inversely proportional to the photon energy $E:\lambda/nm=1.24/(E/keV)$) of radiation to be reflected Accordingly, monochromator 60 Bragg-reflects radiation of wavelength $\lambda$ that intercepts surface 61 at an angle of incidence equal to $\sin^{-1}(\lambda/(2*d))$.

The Bragg reflection monochromatizes the received radiation such that the reflected radiation is of a wavelength substantially equal to $\lambda$, and of an energy corresponding to $\lambda$. In practice, the wavelength/energy bandwidth of the reflected radiation may be 3% to 5%, depending on a mosaicity of the diffracting material and/or the openings of blocking devices 51 and 52.

The above-described geometric relationship between ring anode 42 and monochromator 60 is intended to provide a conical radiation path with an approximately 30° angle of convergence and to provide a monochromatizing reflection such as a Bragg reflection. Specific geometric relationships between anode 42 and monochromator 60 may depend on the desired angle of convergence and the magnitudes of desired diffraction angles. Arrangements according to some embodiments may therefore provide angles of convergence and monochromatizing reflections that are difficult, if not impossible, to achieve using a point radiation source.

Monochromatized radiation 64 passes through an aperture of blocking device 52 and travels along a substantially convergent three-dimensional path to target 55. Blocking devices 52 and 62 may be positioned in order to block non-monochromatized radiation from passing through blocking device 52.

In contrast to an ideal crystal like Diamond or Silicon, HOPG and other crystalline materials usable in some embodiments are mosaic crystals. According to some embodiments, the mosaicity is less than 5°, and may be 0.5°. This mosaicity allows the crystalline reflector material to reflect monochromatic X-radiation over a certain range of incidence angles, i.e. to reflect X-radiation of a certain source solid angle onto target 55. In this regard, a focus of the radiation may comprise a point in space or a larger area. A size and location of the focus may be determined by many factors, including radiation energy, and the geometries and lattice plane distances of the reflector materials 61. A detailed explanation of Bragg-Brentano focusing according to some embodiments will be provided below with respect to FIG. 8.

The radiation that exits blocking device 52 might not terminate at target 55. Rather, the radiation may continue thereafter, becoming further attenuated and unfocused as its distance from target 55 increases. In some embodiments, the divergence of the radiation from target 55 roughly mirrors its convergence thereto.

Some embodiments use phenomena other than or in addition to those described above to monochromatize and/or focus X-ray radiation emitted from anode 42. These phenomena include, but are not limited to, other types of diffraction using crystal lattices (e.g. Laue diffraction), total reflection at grazing angles (e.g. Kirkpatrick-Baez: P. Kirkpatrick and A. V. Baez, J. Opt. Soc. Am. 38 (1948) 766), and multi-layer diffraction (e.g. M. Schuster and H. Göbel, J. Phys. D: Appl. Phys. 28 (1995) A270).

Monochromatization and/or focusing of radiation may provide more efficient and accurate radiation therapy than previously available. Particularly, some embodiments produce a focused radiation beam having a narrow band of photon energies. Moreover, some embodiments provide radiation having a significantly greater flux density at an internal target than at a patient's skin. Penetration of an X-radiation beam according to some embodiments may therefore be controlled to efficiently deliver tissue damaging mechanisms to precise locations within a patient, while minimizing damage to other locations.

Figure 6:
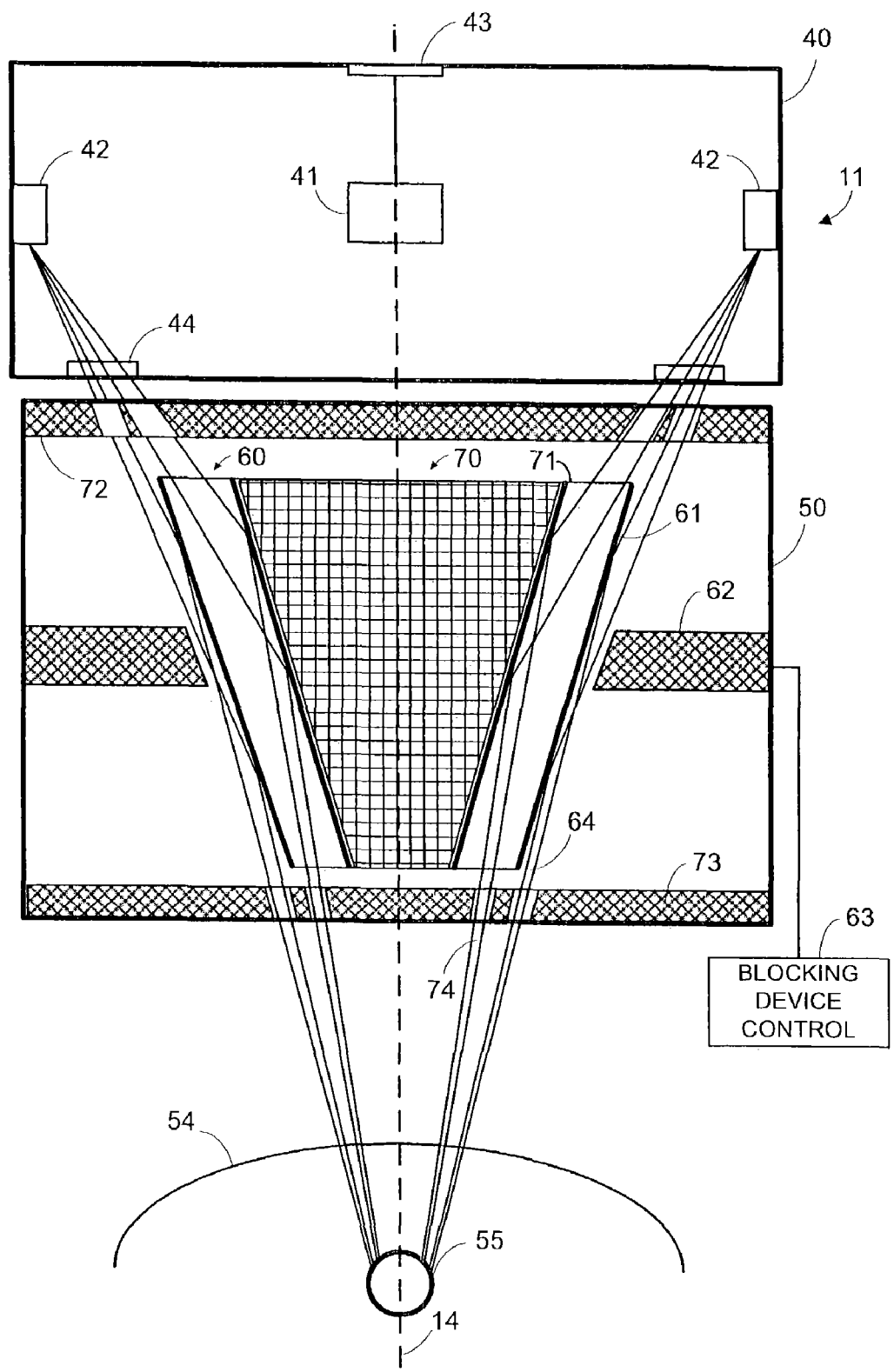
FIG. 6 is a longitudinal cross-section illustrating internal elements of a therapy head according to some embodiments, the therapy head including an annular anode and two monochromators each having one external conical reflector surface.

FIG. 6 is a longitudinal cross-section of therapy head 11 according to some embodiments. Therapy head 11 of FIG. 6 includes previously-undescribed elements 70 through 74. Initially, monochromator 70 is conical and coaxial with monochromator 60. Monochromator 70 comprises surface 71 of diffracting material. The material of surface 71 may be different from or identical to the material of surface 61. Moreover, monochromators 60 and 70 may be integrally formed.

Blocking device 72 defines two coaxial conical openings. An outermost opening allows a first portion of radiation from window 44 to intercept surface 61, while an innermost opening allows a second portion of radiation to intercept surface material 71. As described above with respect to FIG. 5, the elements of therapy head 11 may be configured such that the first portion of radiation intercepts surface 61 at a Bragg angle corresponding to the material of surface 61 and to a desired energy of monochromatization. Similarly, the second portion of radiation intercepts surface 71 at a Bragg angle corresponding to the material of surface 71 and to a desired energy.

For a given desired energy, the Bragg angle corresponding to the material of surface 71 may be larger than the Bragg angle corresponding to the material of surface 61 due to smaller lattice plane distances of the former material. Alternatively, the materials may be identical, however using a higher-order reflection of the material of surface 71. In some embodiments, the materials are identical and the elements of therapy head 11 are arranged such that the radiation intercepts surface 61 and surface 71 at substantially identical angles.

Monochromatized radiation 64 and 74 passes through corresponding coaxial openings of blocking device 73 and on to target 55. Blocking device 62 and blocking device 73 may substantially block non-monochromatized radiation from exiting from housing 50. Monochromatized radiation 64 and 74 may also be focused on target 55 as a result of Bragg-Brentano focusing mechanisms.

Figure 7:
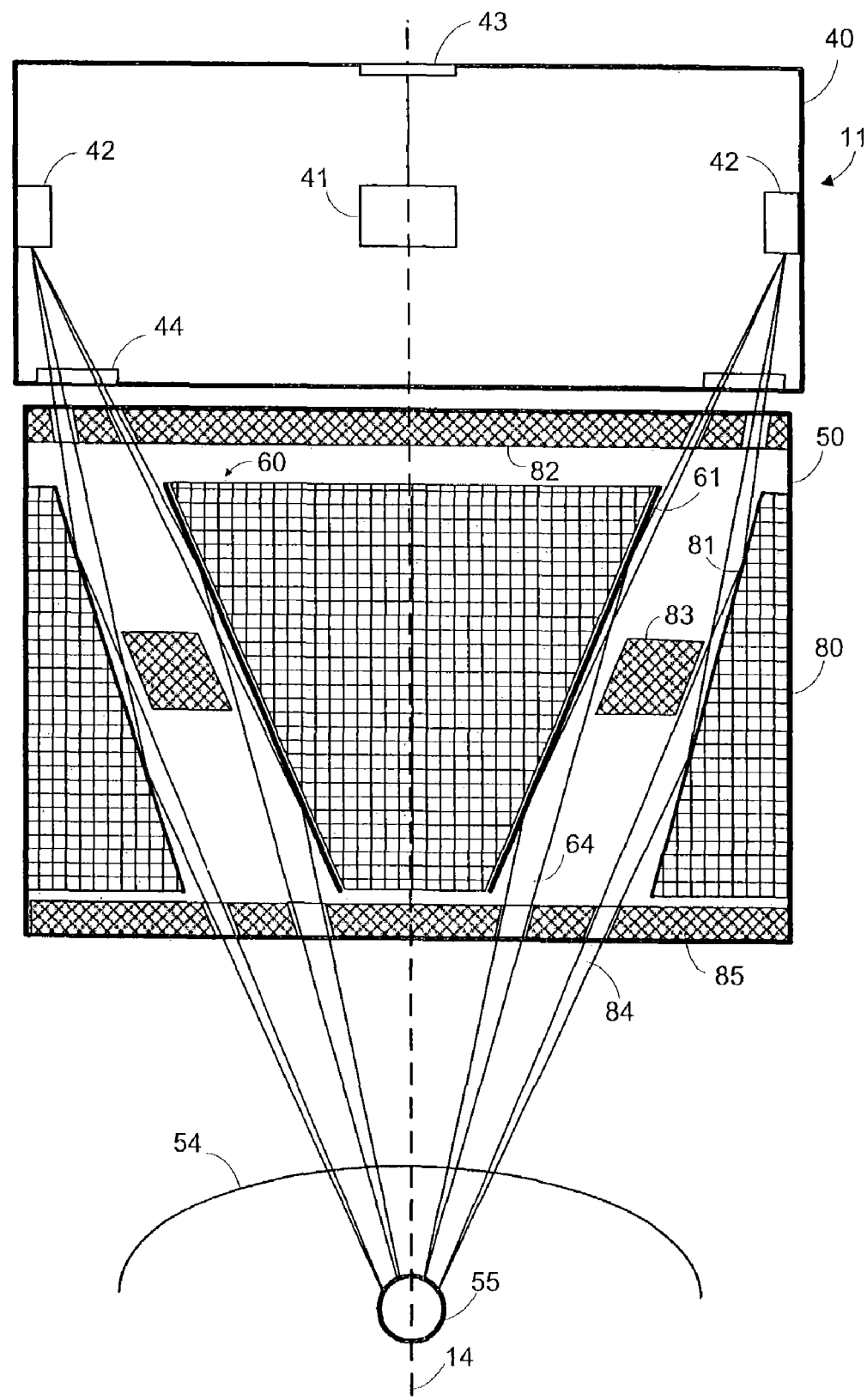
FIG. 7 is a longitudinal cross-section illustrating internal elements of a therapy head according to some embodiments, the therapy head including an annular anode, a monochromator with one external conical reflector surface, and a monochromator with one internal conical reflector surface.

FIG. 7 illustrates a system using monochromator 80 in conjunction with monochromator 60. Monochromator 80 of FIG. 7 comprises a solid ring defining a conical opening. Interior surface 81 of monochromator 80 faces and is separate from surface 61 of monochromator 60. Interior surface 81 also includes a layer of diffracting material. Blocking device 82 includes two concentric conical openings, With an innermost opening allowing a first portion of radiation from window 44 to intercept material 61, and with an outermost opening allowing a second portion of radiation to intercept material 81.

The elements of therapy head 11 may be configured such that the first portion of radiation intercepts surface 61 at a Bragg angle corresponding to the material of surface 61 and to a desired energy of monochromatization, and such that the second portion of radiation intercepts surface 81 at a Bragg angle corresponding to the material of surface 81 and to a desired energy. The Bragg angles may be identical in a case that the two materials and the desired photon energies are identical, and may be different in a case that the two materials possess differing interplanar distances. As mentioned above, the Bragg angles may also be different in a case that the two materials are identical, but either different orders of reflection or desired photon energies are associated with surface 61 and surface 81 in such a case.

Blocking device 83 comprises a conical ring for ensuring that only monochromatized radiation passes to blocking device 85. Blocking device 83 may be movable along a major axis of monochromator 60 under control of a control device (not shown). Moreover, a diameter of an opening of blocking device 83 may increase with movement toward tube 40. Monochromatized radiation 64 and monochromatized radiation 84 pass through corresponding coaxial openings of blocking device 85. Blocking devices 83 and 85 may therefore block all but monochromatized radiation from passing to target 55.

Figure 8:
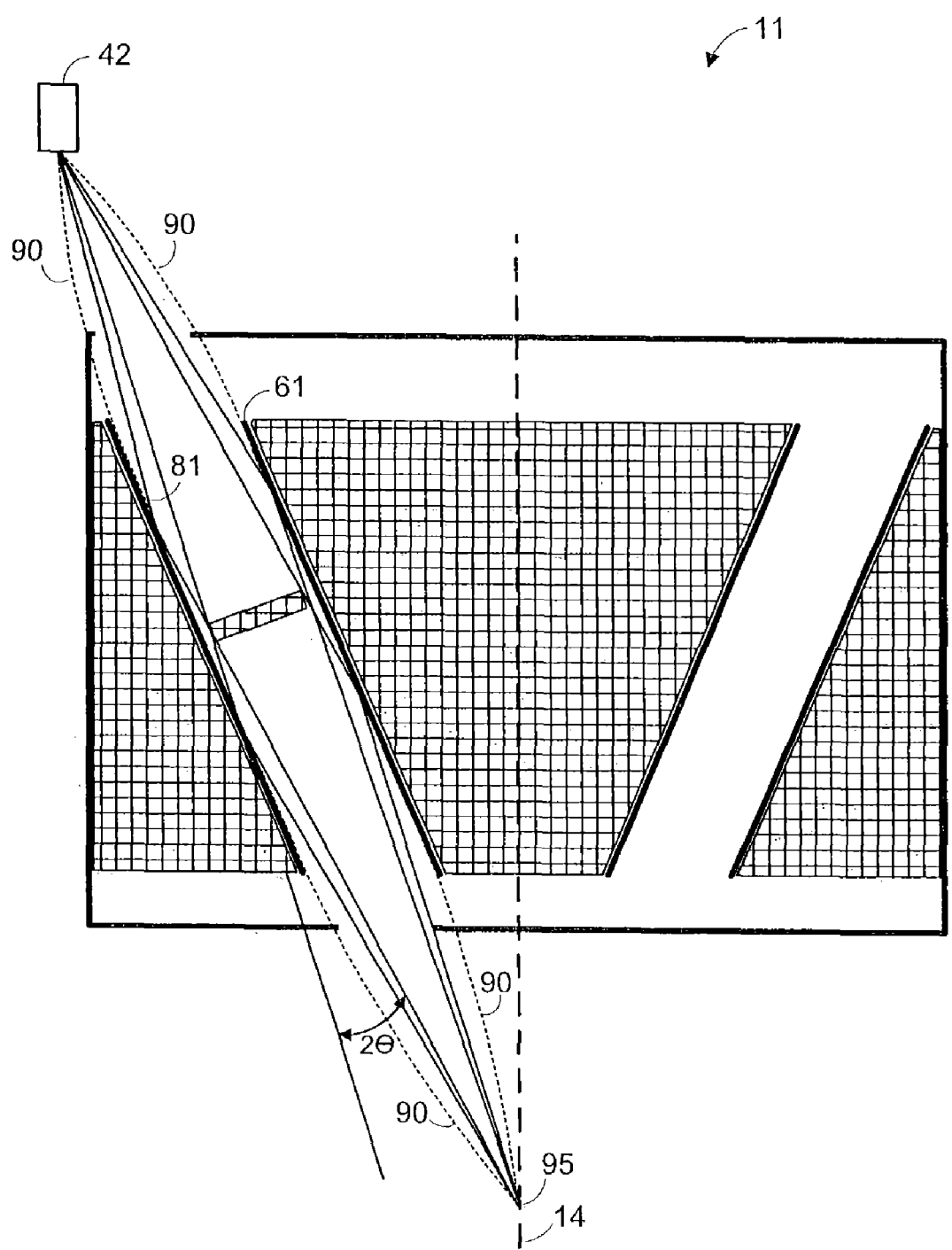
FIG. 8 is a longitudinal cross-section of a portion of a therapy head illustrating Bragg-Brentano focusing according to some embodiments, the therapy head including an annular anode, a monochromator with one external conical reflector surface, and a monochromator with one internal conical reflector surface.

FIG. 8 is a longitudinal cross-section of some elements of therapy head 11 according to FIG. 7. FIG. 8 will be used to describe Bragg-Brentano focusing according to some embodiments.

As shown, surfaces 61 and 81 are tangent to Rowland circle 90. Rowland circle 90 of FIG. 8 represents the reflection points of all X-ray beams emitted from an area of anode 42 that correspond to the same Bragg angle of interest. Each of the represented beams therefore corresponds to a same photon energy and wavelength.

Crystallites within surfaces 61 and 81 will possess a mosaicity of 0.5° in a case that the surfaces are composed of (00.1) oriented HOPG. As a result, all X-rays that are incident to either of surfaces 61 or 81 at an angle of +/−0.5° will encounter a reflecting crystal. Such reflections result in the focusing of the beams as shown on focus 95. The mosaicity, the value d of the diffracting material, and the lengths of surfaces 61 and 81 may therefore operate in harmony to deliver monochromatized, high-intensity radiation to focus 95.

Generally, those in the art will appreciate that various adaptations and modifications of the above-described embodiments can be configured without departing from the scope and spirit of the claimed invention. For example, heavy-element contrast agents may be introduced within target 55 to increase the effective dose absorbed by target 55 in the presence of KVR. A contrast agent may include rare earth elements and/or elements having a K absorption edge energy that is just below a characteristic K line energy of a material of the ring anode. In one particular example, the ring anode comprises tungsten and the contrast agent comprises at least one of erbium, holmium, dysprosium, terbium, gadolinium, europium, samarium, neodymium, praseodymium, cerium, and lanthanum.

Some embodiments include two or more coaxial or otherwise disposed ring anodes and a dedicated monochromator to Bragg-reflect radiation released from each ring anode. Some embodiments may utilize two or more ring anodes composed of different materials. Different radiation energies and resulting penetration depths may therefore be achieved by applying different anode voltages to different ones of the ring anodes. Moreover, a point focus radiation source may be positioned to emit a thin beam along axis 14 of monochromator 60 for alignment purposes.

Some embodiments utilize rotationally-symmetric elements that require adjustments only along the rotational axis. In some embodiments, a monochromator may be moved in and out of an operational position to provide a "filtered radiation" mode and a "monochromatized radiation" mode.

Therefore, it is to be understood that, within the scope of the appended claims, embodiments of the invention may be practiced other than as specifically described herein.

What is claimed is:

1. An apparatus comprising:
   a radiation source to emit radiation from at least a first location and a second location, the first and second locations being separated by a first distance; and
   a monochromator comprising a surface of diffracting material, the surface comprising a third location and a fourth location separated by a second distance, the second distance being less than the first distance,
   wherein the third location is to receive the radiation emitted from the first location and wherein the fourth location is to receive the radiation emitted from the second location.

2. An apparatus according to claim 1, wherein the radiation source comprises a ring anode.

3. An apparatus according to claim 2, wherein an outer diameter of the ring anode is greater than a largest outer diameter of the monochromator.

4. An apparatus according to claim 2, wherein the radiation source further comprises a ring cathode concentric with the ring anode.

5. An apparatus according to claim 2, wherein the radiation source further comprises a cathode adapted to move along a circumference of the ring anode.

6. An apparatus according to claim 2, wherein the radiation source further comprises a plurality of cathodes located at a respective plurality of positions adjacent to the ring anode.

7. An apparatus according to claim 2, wherein the radiation source comprises a plurality of ring anodes.

8. An apparatus according to claim 7, wherein one of the plurality of ring anodes is composed of a material different from a material of another one of the ring anodes.

9. An apparatus according to claim 2, wherein the ring anode is a transmission anode.

10. An apparatus according to claim 1, wherein the radiation source is adapted to move along a continuous path and to emit the radiation from a plurality of locations on the continuous path.

11. An apparatus according to claim 1, wherein the radiation source comprises a plurality of radiation sources.

12. An apparatus according to claim 1, the radiation from the first location to intercept the surface of diffracting material at a first angle of incidence, the first angle of incidence substantially equal to a first Bragg angle corresponding to the diffracting material.

13. An apparatus according to claim 12, the diffracting material to substantially monochromatize the radiation from the first location.

14. An apparatus according to claim 13, the diffracting material to substantially focus the radiation from the first location onto a target.

15. An apparatus according to claim 13, further comprising:
   one or more blocking devices to prevent substantially all but monochromatized radiation from traveling toward a target.

16. An apparatus according to claim 15, the diffracting material to substantially focus the radiation from the first location onto the target.

17. An apparatus according to claim 15, wherein one or more of the one or more blocking devices are movable.

18. An apparatus according to claim 15, wherein one or more of the one or more blocking devices comprise an annular ring.

19. An apparatus according to claim 12, the diffracting material arranged in highly-oriented layers and adapted to substantially reflect X-ray radiation.

20. An apparatus according to claim 19, wherein a mosaicity of the diffracting material is less than 5°.

21. An apparatus according to claim 20, wherein a mosaicity of the diffracting material is equal to 0.5°.

22. An apparatus according to claim 19, wherein the diffracting material comprises Highly Oriented Pyrolytic Graphite (HOPG) and where the material is oriented (00.1) on the surface of the monochromator.

23. An apparatus according to claim 22, wherein HOPG (00.2), HOPG(00.4), or HOPG(00.6) reflections are used to direct the X-radiation to a target.

24. An apparatus according to claim 12, wherein the lattice plane distance of the diffracting material is equal to d, wherein a wavelength of the radiation is equal to $\lambda$, and wherein the first Bragg angle is equal to $\sin^{-1}(\lambda/(2*d))$.

25. An apparatus according to claim 12, further comprising a second monochromator, the second monochromator comprising a second surface of second diffracting material, wherein radiation from the radiation source is to intercept the second surface of second diffracting material at a second angle of incidence, the second angle of incidence substantially equal to a second Bragg angle corresponding to the second diffracting material.

26. An apparatus according to claim 25, wherein a lattice plane distance of the diffracting material is equal to $d_1$, wherein a wavelength of the radiation is equal to $\lambda$, wherein the first Bragg angle is equal to $\sin^{-1}(\lambda/(2*d_1))$, wherein a lattice plane distance of the second diffracting material is equal to $d_2$, and wherein the second Bragg angle is equal to $\sin^{-1}(\lambda/(2*d_2))$.

27. An apparatus according to claim 25, wherein the surface comprises a first conical surface, the second surface comprises a second conical surface, and the first conical surface is coaxial with the second conical surface.

28. An apparatus according to claim 12, further comprising a second monochromator, the second monochromator comprising a second surface of the diffracting material, wherein a lattice plane distance of the diffracting material is equal to $d_1$, wherein a wavelength of the radiation is equal to $\lambda$, wherein the first Bragg angle is equal to $\sin^{-1}(\lambda/(2*d_1))$, wherein radiation from the radiation source is to intercept the second surface at a second angle of incidence, and wherein the second angle of incidence is equal to $\sin^{-1}(\lambda n/(2*d_1))$, where n is an integer greater than 1.

29. An apparatus according to claim 1, wherein the radiation primarily comprises KVR.

30. An apparatus according to claim 1, wherein the surface of diffracting material is substantially conical, and further comprising:

at least one blocking device defining a conical opening, the at least one blocking device being movable along a longitudinal axis of the conical opening, and wherein a diameter of the conical opening increases with movement of the at least one blocking device toward the radiation source.

31. An apparatus according to claim 1, wherein the monochromator comprises:

a second surface facing and separate from the surface of diffracting material, the second surface comprising the diffracting material, and the second surface to intercept a portion of the emitted radiation at a Bragg angle corresponding to the diffracting material.

32. An apparatus comprising:
a ring anode to emit radiation; and
a conical monochromator to monochromatize the emitted radiation.

33. An apparatus according to claim 32, wherein an outer diameter of the ring anode is greater than an outer diameter of a base of the monochromator.

34. An apparatus according to claim 32, further comprising a ring cathode concentric with the ring anode.

35. An apparatus according to claim 32, the apparatus further comprising:
a cathode adapted to move along a circumference of the ring anode.

36. An apparatus according to claim 32, the apparatus further comprising:
a plurality of cathodes located at a respective plurality of positions adjacent to the ring anode.

37. An apparatus according to claim 32, further comprising a plurality of ring anodes concentric with the ring anode.

38. An apparatus according to claim 37, wherein one of the plurality of ring anodes is composed of a material different from a material of another one of the ring anodes.

39. An apparatus according to claim 32, a surface of the monochromator comprising diffracting material, a portion of the emitted radiation to intercept the surface at a first angle of incidence, the first angle of incidence substantially equal to a first Bragg angle corresponding to the diffracting material.

40. An apparatus according to claim 39, the diffracting material to substantially focus the radiation onto a target.

41. An apparatus according to claim 39, the diffracting material arranged in highly-oriented layers and adapted to substantially reflect X-radiation.

42. An apparatus according to claim 41, wherein a mosaicity of the diffracting material is less than 5°.

43. An apparatus according to claim 42, wherein a mosaicity of the diffracting material is equal to 0.5°.

44. An apparatus according to claim 42, wherein the diffracting material comprises Highly Oriented Pyrolitic Graphite (HOPG) and where the material is oriented (00.1) on the surface of the monochromator.

45. An apparatus according to claim 44, wherein HOPG (00.2), HOPG(00.4), or HOPG(00.6) reflections are used to direct the X-radiation to a target.

46. An apparatus according to claim 39, wherein the lattice plane distance of the diffracting material is equal to d, wherein a wavelength of the radiation is equal to $\lambda$, and wherein the first Bragg angle is equal to $\sin^{-1}(\lambda/(2*d))$.

47. An apparatus according to claim 39, further comprising:

a second conical monochromator, a surface of the second monochromator comprising second diffracting material, a portion of the emitted radiation to intercept the surface of the second monochromator at a second angle of incidence, the second angle of incidence substantially equal to a second Bragg angle corresponding to the second diffracting material.

48. An apparatus according to claim 47, wherein the lattice plane distance of the diffracting material is equal to $d_1$, wherein a wavelength of the radiation is equal to $\lambda$, wherein the first Bragg angle is equal to $\sin^{-1}(\lambda/(2*d_1))$, wherein a lattice plane distance of the second diffracting material is equal to $d_2$, and wherein the second Bragg angle is equal to $\sin^{-1}(\lambda/(2*d_2))$.

49. An apparatus according to claim 47, wherein the conical monochromator and the second conical monochromator are coaxial.

50. An apparatus according to claim 39, wherein the monochromator comprises:

a second surface facing and separate from the surface of diffracting material, the second surface comprising the diffracting material, and the second surface to intercept a portion of the emitted radiation at the first Bragg angle.

51. An apparatus according to claim 39, further comprising a second monochromator, the second monochromator comprising a second surface of the diffracting material, wherein a lattice plane distance of the diffracting material is equal to $d_1$, wherein a wavelength of the radiation is equal to $\lambda$, wherein the first Bragg angle is equal to $\sin^{-1}(\lambda/(2*d_1))$, wherein radiation from the radiation source is to intercept the second surface at a second angle of incidence, and wherein the second angle of incidence is equal to $\sin^{-1}(\lambda n/(2*d_1))$, where n is an integer greater than 1.

52. An apparatus according to claim 32, further comprising:
one or more blocking devices to prevent substantially all but monochromatized radiation from traveling toward a target.

53. An apparatus according to claim 52, wherein one or more of the one or more blocking devices are movable.

54. An apparatus according to claim 52, wherein one or more of the one or more blocking devices comprise an annular ring.

55. An apparatus according to claim 32, further comprising:
at least one blocking device defining a conical opening, the at least one blocking device being movable along a major axis of the conical opening, and wherein a diameter of the conical opening increases with movement of the at least one blocking device toward the ring anode.

56. An apparatus according to claim 32, wherein the ring anode is a transmission anode.

57. An apparatus comprising:
a ring anode radiation source to release radiation; and
one or more blocking devices to substantially block the radiation except for a portion of the radiation traveling along a substantially convergent three-dimensional path.

58. An apparatus according to claim 57, wherein the radiation source further comprises a ring cathode concentric with the ring anode.

59. An apparatus according to claim 57, wherein the radiation source further comprises a cathode adapted to move along a circumference of the ring anode.

60. An apparatus according to claim 57, wherein the radiation source further comprises a plurality of cathodes located at a respective plurality of positions adjacent to the ring anode.

61. An apparatus according to claim 57, wherein the radiation source comprises a plurality of concentric ring anodes.

62. An apparatus according to claim 61, wherein one of the plurality of ring anodes is composed of a material different from a material of another one of the ring anodes.

63. An apparatus according to claim 57, wherein the ring anode is a transmission anode.

64. An apparatus according to claim 57, wherein the radiation source is adapted to move along a continuous path and to emit the radiation from a plurality of locations on the continuous path.

65. An apparatus according to claim 57, wherein the radiation source comprises a plurality of radiation sources.

66. An apparatus according to claim 57, wherein one or more of the one or more blocking devices is to define a conical beam path converging to a target.

67. An apparatus according to claim 66, wherein the one or more of the one or more blocking devices defines a conical opening aligned to the target and to block radiation released from the radiation source that does not travel toward the target.

68. An apparatus according to claim 57, wherein one or more of the one or more blocking devices comprise an annular ring.

69. An apparatus according to claim 57, further comprising:
a filter to substantially filter radiation having energies less than a threshold energy.

70. An apparatus according to claim 57, wherein the portion of the radiation primarily comprises kilovoltage radiation.

71. A method comprising:
introducing a contrast agent within a target; and
operating a therapy head to deliver monochromatized radiation to the target, the therapy head comprising a ring anode to emit radiation and a conical monochromator to monochromatize the emitted radiation.

72. A method according to claim 71, wherein the contrast agent comprises rare earth elements.

73. A method according to claim 71, wherein the contrast agent comprises elements having a K absorption edge energy that is just below a characteristic K line energy of a material of the ring anode.

74. A method according to claim 73, wherein the ring anode comprises tungsten and wherein the contrast agent comprises at least one of erbium, holmium, dysprosium, terbium, gadolinium, europium, samarium, neodymium, praseodymium, cerium, and lanthanum.

* * * * *